(12) United States Patent
Porcher

(10) Patent No.: US 7,758,620 B2
(45) Date of Patent: Jul. 20, 2010

(54) DEVICE FOR CONNECTING A SCREW TO A SUPPORT PLATE

(75) Inventor: Robert Porcher, Yzernay (FR)

(73) Assignee: Stryker Trauma SA (CH)

( * ) Notice: Subject to any disclaimer, the term of this patent is extended or adjusted under 35 U.S.C. 154(b) by 1012 days.

(21) Appl. No.: 10/999,132

(22) Filed: Nov. 29, 2004

(65) Prior Publication Data

US 2005/0143742 A1 Jun. 30, 2005

Related U.S. Application Data

(63) Continuation-in-part of application No. PCT/FR03/02779, filed on Sep. 22, 2003.

(30) Foreign Application Priority Data

Sep. 24, 2002 (FR) .................................. 02 11802

(51) Int. Cl.
*A61B 17/80* (2006.01)

(52) U.S. Cl. ........................ 606/290; 606/289

(58) Field of Classification Search .............. 606/60, 606/69–71, 289, 290; 411/371.2, 372, 352, 411/353, 191, 197, 198
See application file for complete search history.

(56) References Cited

U.S. PATENT DOCUMENTS

| | | | |
|---|---|---|---|
| 5,531,554 A | 7/1996 | Jeanson et al. | |
| 5,954,722 A | 9/1999 | Bono | |
| 6,193,721 B1 | 2/2001 | Michelson | |
| 6,235,003 B1 | 5/2001 | Dysarz | |
| 6,454,771 B1 | 9/2002 | Michelson | |
| 6,572,622 B1 | 6/2003 | Schafer et al. | |
| 6,575,975 B2 * | 6/2003 | Brace et al. | 606/69 |
| 6,695,846 B2 * | 2/2004 | Richelsoph et al. | 606/71 |
| 6,730,091 B1 | 5/2004 | Pfefferle et al. | |
| 7,229,443 B2 * | 6/2007 | Eberlein et al. | 606/69 |
| 7,273,481 B2 * | 9/2007 | Lombardo et al. | 606/69 |
| 7,303,564 B2 * | 12/2007 | Freid et al. | 606/69 |
| 2001/0037112 A1 | 11/2001 | Brace et al. | |
| 2003/0187440 A1 | 10/2003 | Richelsoph et al. | |
| 2003/0187442 A1 | 10/2003 | Richelsoph et al. | |

(Continued)

FOREIGN PATENT DOCUMENTS

CA 2 471 843 A1 7/2003

(Continued)

*Primary Examiner*—Thomas C Barrett
*Assistant Examiner*—Andrew Yang
(74) *Attorney, Agent, or Firm*—Lerner, David, Littenberg, Krumholz & Mentlik, LLP

(57) ABSTRACT

The invention relates to a device which is used for solidly connecting a part such as a plate to an underlying support using at least one fixing element such as a screw. According to the invention, said fixing element takes the form of a threaded rod a screw which passes through a hole housing a ring belonging to the part, such that it is screwed into the support material. The inventive device is characterized in that the above-mentioned ring is a constriction ring comprising a non-circular outer profile which co-operates with the non-circular inner profile of the hole, which is in the part. In this way, when the ring is rotated in the hole and wedged in place therein, it is constricted, thereby blocking the threaded rod against movement with respect to the plate.

19 Claims, 6 Drawing Sheets

U.S. PATENT DOCUMENTS

| | | |
|---|---|---|
| 2005/0043736 A1 | 2/2005 | Mathieu et al. |
| 2007/0123879 A1* | 5/2007 | Songer et al. .................. 606/69 |

FOREIGN PATENT DOCUMENTS

| | | |
|---|---|---|
| DE | 9308944 | 9/1993 |
| DE | 100 39 767 A1 | 7/2001 |
| FR | 2 674 118 A1 | 9/1992 |
| FR | 2 739 151 A1 | 3/1997 |
| FR | 2 744 011 A1 | 8/1997 |
| FR | 2 790 198 A1 | 9/2000 |
| FR | 2792185 | 10/2000 |
| WO | WO-94-07040 | 3/1994 |
| WO | 9909903 | 3/1999 |
| WO | WO 99/59492 A1 | 11/1999 |
| WO | WO-03/055401 | 7/2003 |
| WO | WO-2004/086990 A1 | 10/2004 |

* cited by examiner

FIGURE 4
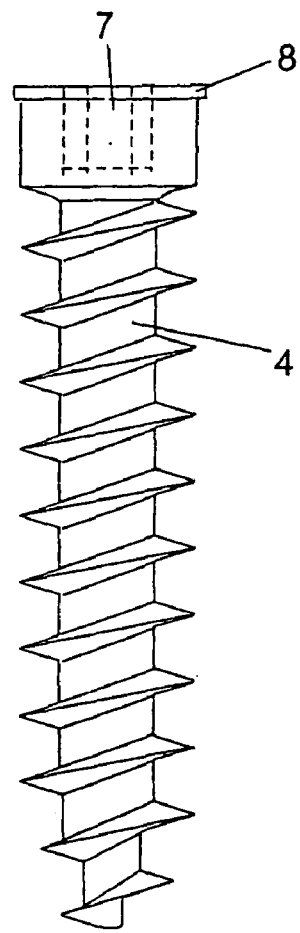
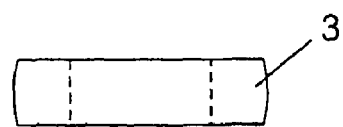
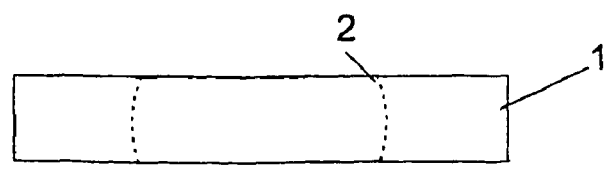

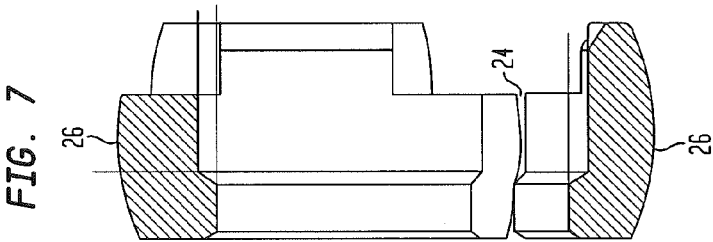
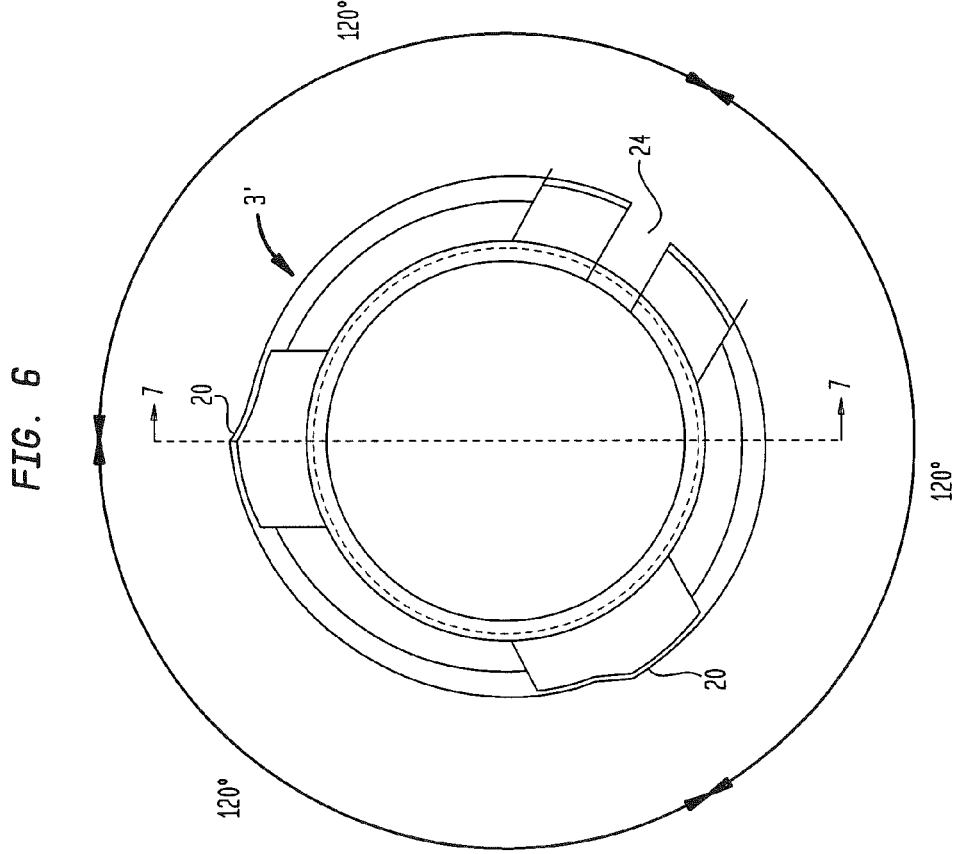

DEVICE FOR CONNECTING A SCREW TO A SUPPORT PLATE

CROSS-REFERENCE TO RELATED APPLICATIONS

This application is a continuation-in-part of WO 2004/028334 A2 filed Sep. 22, 2003, designating the United States, which claimed priority of FR 02/11802 filed Sep. 24, 2002.

BACKGROUND OF THE INVENTION

The present invention relates to a device for solidly connecting a part, such as an osteosynthesis plate, to a support, such as a bone mass. The device has at least one fixing component taking the form of a threaded rod or screw passing through an aperture or hole in the plate. The hole includes a ring belonging to the plate such that it can lock the screw after it is screwed into the support material. The plate can be in the form of a spherical acetabular cup shell for contacting the natural acetabulum.

Screw-and-plate osteosynthesis systems must allow immobilizing one or more bone fragments in reference to others. It is known to use spherical-head screws cooperating with a spherical housing housed in a plate and bringing the plate into compression over the bone until the friction of the plate on the bone stabilizes the assembly. These assemblies allow choice of the angle of implantation of screws during the operation and causing a return movement and a compression of a detached bone fragment. Certain of these systems allow, due to the oblong shape of the aperture, made in the plate, compression of one bone fragment on another. The shortcoming of these systems is their low resistance to compression stresses exerted parallel to the plane of the plate.

Use is also known of a second generation of screw-and-plate systems called monoaxial-locking and polyaxial-locking systems in which the strength of the assembly no longer depends on compression of the plate on the bone but on a fixation of the screw in the plate. These systems allow achieving assembly away from the bone with, for the more elaborate ones, the possibility of choosing the angle of implantation of screws during the operation while achieving strength sufficient for postoperative stresses.

One example of monoaxial-locking device is described in patent FR-A-2,739,151. One such device comprises a plate traversed by tapped tapered holes in which are wedged the tapered threaded heads of the screws at the end of tightening. One such system that achieves locking by wedging of a tapered thread into a tapped tapered hole has, as a problem, the fact that as the screw is engaged simultaneously in the plate and in the bone, the possible distance between plate and bone may no longer be reduced. Drawing back a bone fragment is thus impossible. Because of this, the distance between the plate and the bone must be set before the installation of the screw, which is sometimes difficult.

In existing monoaxial mechanisms, bone anchoring is sometimes improved by the introduction of screws with the axes between them not being parallel. However, unlike the divergent course a tension normal to the plate does not cause the latter to pull out. To achieve such orientation of the screws, the plate to be fixed to the support can be provided with holes with axis non-orthogonal to the surface of the plate such that the orientation of the screw is provided by the orientation of the hole in the plate. The surgeon then has no freedom concerning the orientation of the screw to be fixed. This predetermined orientation may sometimes prove to be incompatible with anatomical constraints. Moreover, existing devices do not allow the plate and the support, such as the bone, to be brought together optimally without impairing coaxiality between axis of the plate and axis of the internal thread.

One example of a polyaxial locking mechanism is specifically described in patent FR-A-2,790,198. One such device comprises a plate equipped with a ring expanding radially during the threading of the screw to allow immobilization of the ring and then of the screw inside the hole of the plate. The expansion of the ring is obtained by a tapered threading of the screw and of the internal bore of the ring. A similar system is also shown in U.S. Pat. No. 5,954,722.

A system is likewise known through patent DE 100 39 767 comprising a ring with spherical external shape being able to be adjusted inside a plate comprising a spherical housing. The ring is traversed by a screw, whose head is housed in a bore of the ring. No blocking system is described for the screw.

U.S. Pat. Nos. 6,235,003 and 6,575,975 relate to a system comprising a ring whose outside shape is spherical, orientable inside a plate comprising a spherical housing. The ring is traversed by a screw, whose head is housed in a cylindrical bore of the ring. Locking is obtained by expansion of the head of the screw using an additional tapered screw.

Finally, U.S. Pat. No. 5,531,554 relates to a system comprising a malleable-collar screw. The collar is restricted when it is driven into a tapered hole on the plate until it spreads beyond the said hole, since it expands due to elasticity to prevent the screw from being removed. Return movement of the collar of the screw to its initial shape also inhibits axial displacement of the screw in the sense of an extraction of the screw from the bore in the plate.

It should be noted that other systems achieve locking by introduction under force of the threaded head of the screw in the housing of the plate. The force necessary for the deformation of the material in the housing is significant. Moreover, risks from detachment of metal particles cannot be ruled out.

SUMMARY OF THE INVENTION

One aspect of the present invention is thus to propose a device for solidly connecting a part, such as a bone plate, on a support, such as a bone, in which the design allows optimally bringing together the plate and the support, pre-operative orientation of the screw, and easy installation and removal of the assembly while offering good resistance to pull out and to the stresses exerted parallel to the plane of the plate.

For this purpose, the invention has as object a device for solidly connecting a part, such as an osteosynthesis plate, to a support, such as a bone mass, using at least one fixing element in the form of a threaded rod or screw passing through a hole or aperture housing a ring. The screw, of the device is for screwing into the support material such as a bone screw. The ring is a constriction ring whose non-circular external profile cooperates with the non-circular internal profile of the hole or aperture in the plate by causing, at the time of rotational driving of the ring in the hole, at the same time as immobilization by wedging of the ring in the hole, constriction of the ring ensuring the immobilization of the threaded screw such as by clamping around the head of the screw. In other words the rotation of the non-circular split ring in the non-circular plate hole causes the inner diameter of the split ring to be reduced around the screw or rod.

One such device allows easy installation of the screw that is not, before constriction of the ring, in contact with the ring. Moreover, bringing together the plate and the bone or underlying support is done simply by screwing, the distance between plate and support being able to be adjusted as needed. Finally, locking is done using a simple tool that ensures rotational driving of the ring.

The invention has as a further aspect a method of installation of a device for solidly connecting a part, such as an osteosynthesis plate, on a support, such as a bone mass, using at least one fixing element in the form of a threaded rod or screw passing through a hole or aperture in the plate the hole housing a ring for clamping the head of the screw part to be screwed into the support material. The method consists of introducing the threaded rod or screw into the ring itself disposed in the hole in the part, then to drive the threaded screw to its final screwed in position and then to rotationally drive or turn the ring to ensure by constriction of the ring around the threaded rod or screw to immobilize the threaded rod in the hole.

BRIEF DESCRIPTION OF THE DRAWINGS

The invention will be well understood by reading the following description of embodiments, in reference to the included drawings in which:

FIG. 4 is a front view partially in section of the device of FIG. 1 with the constituent elements unassembled;

FIG. 6 is a top view of an alternate embodiment of the constriction split-ring of the present invention FIG. 7 is a cross-sectional view of the alternate split ring shown in FIG. 6.

DETAILED DESCRIPTION

Figure 1:
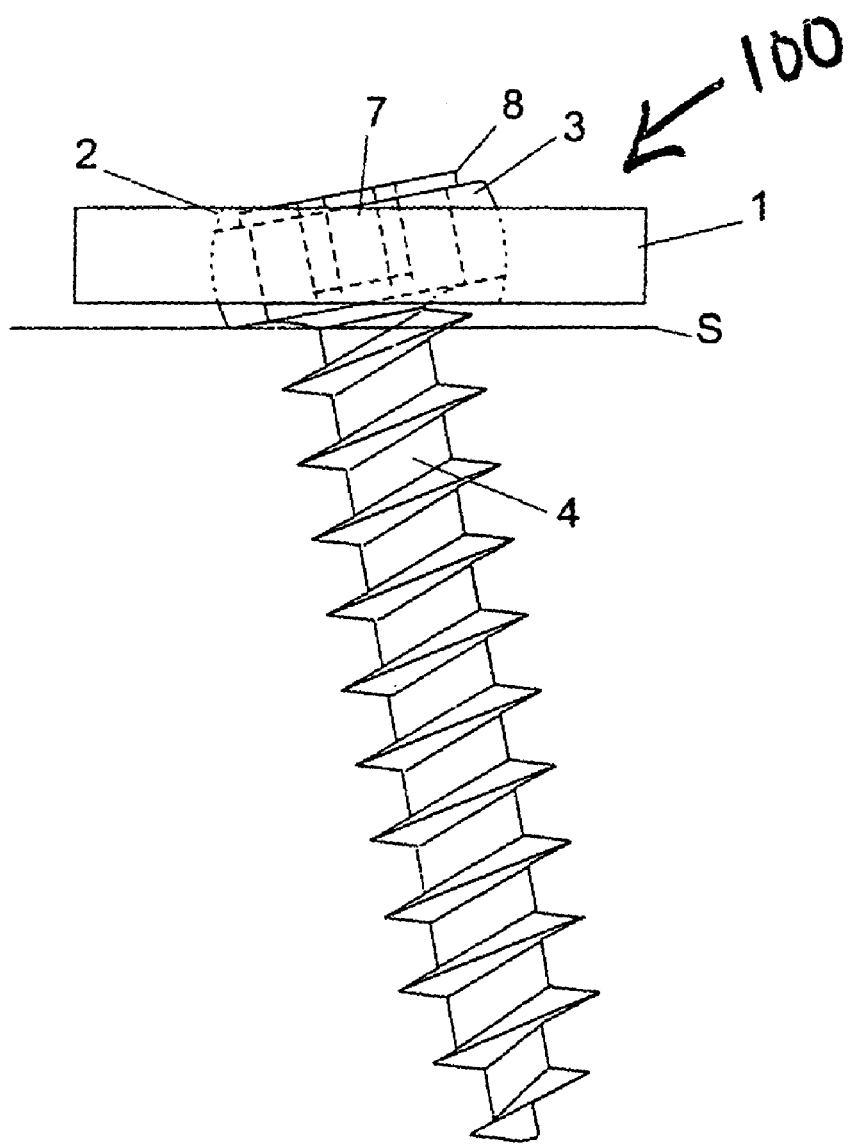
FIG. 1 is a front view partially in section of the connection device of the present invention in the assembled state.
Figure 2:
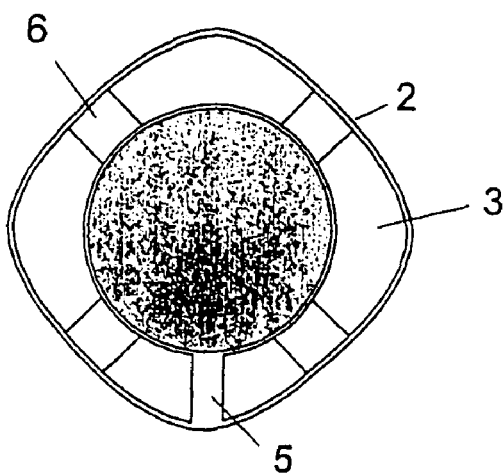
FIG. 2 is a top view of the non-circular ring in its non-circular hole in the absence of any constriction of the ring on the screw.
Figure 3:
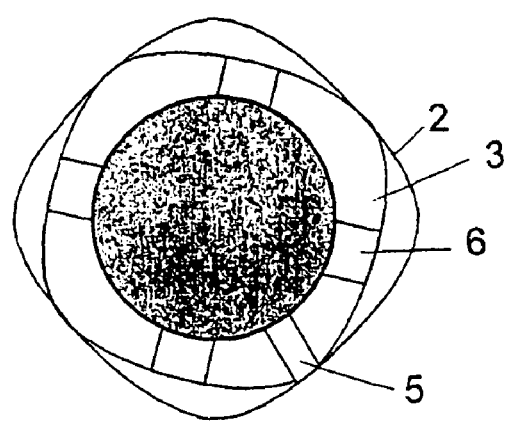
FIG. 3 is a top view of the ring in its hole in position of constriction of the ring on the screw.

Referring to FIG. 1 there is shown the connection device of the present invention generally denoted as 100, comprising a part 1 able to be solidly connected on a support S using at least one fixing element 4. As mentioned above, this device is more specifically intended for the medical field. In this case, the part 1 is an implant generally taking the form of a plate and the support S is at least one bone. Fixing the element 4 for its part comprises a rod or screw threaded over at least part of its length. Rod or screw 4, which ensures the solid connection of the part 1 on the support S, passes through a hole 2 in the plate or part 1 and is anchored on the support S. The hole 2 of this part 1 is provided with a ring 3 traversed by the fixing element 4. The present invention, ring 3 can be constricted at the time of its rotational drive into the hole 2, this constriction of the inner diameter of ring 3 ensuring, generally by cooperation with the head or end part of the thread of the screw or rod 4, immobilization of the threaded rod or screw 4 at the same time as immobilization by wedging ring 3 in the hole 2. This immobilization by wedging is achieved by friction of the external surface of the ring 3 against the internal surface of the hole 2. In effect, the non-circular external profile of the ring 3 cooperates with the non-circular internal profile of the hole 2 in the part 1, such as a bone plate to cause, at the same time as the constriction of the ring, the wedging of the ring 3 in the hole 2. It should be noted that the term circular must be understood in its strictest sense, that is to say where all points are equidistant from a fixed point. An example of possible embodiment of one such profile is specifically given in FIGS. 2 and 3. Profiles closer to circular profile may also be envisaged as shown in FIGS. 6 thru 8.

Figure 8:
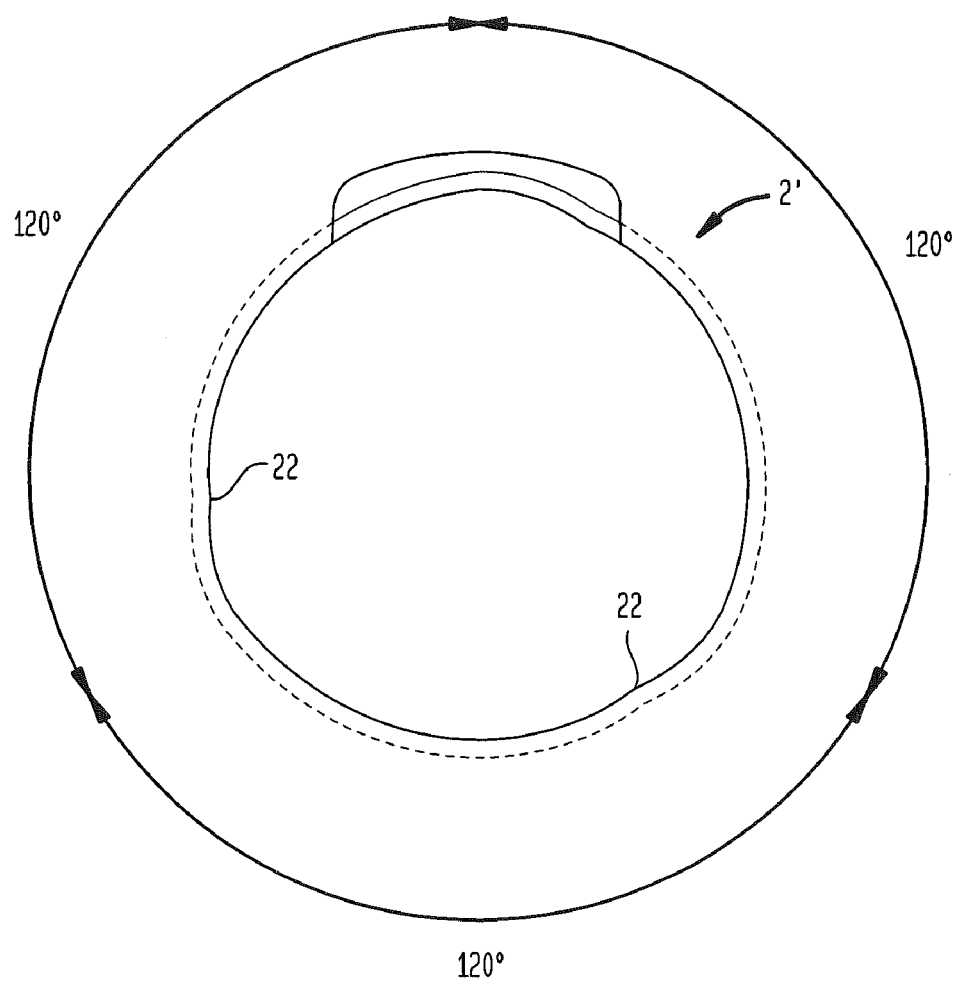
FIG. 8 is a top view of an aperture or hole in the plate showing a complimentary non-circular cross-section for use with the rings of FIGS. 6 and 7.

Alternate non-circular rings 3' are shown in FIGS. 6 thru 8. The ring of FIG. 6 and the complimentary aperture or hole in plate 1 shown in FIG. 8 disclose an alternate non-circular design. Unlike the design of FIGS. 2 and 3 which have generally polygonal cross-sections the designs of FIGS. 6 thru 8 have radially offset portions 20 which interact with radially offset portions 22 of the plate hole of FIG. 8 to cause contraction of slot 24. In this embodiment the radial offsets extend around 120 degrees of the entire circumference of the outer surface of the split ring or the inner surface of the plate aperture. As in the preferred embodiment, split ring 31 may have arcuate outer surfaces 26 to engage within internal part-spherical surfaces of the aperture in the bone plate. Also, a profile comprising two successive spiral parts may be envisaged for the external profile of the ring and internal profile of the hole 2. These profiles may or may not be identical in shape. To facilitate constriction or circular narrowing of the ring 3 around the rod 4, this ring 3 is slotted. The slot is more specifically shown as 5 in FIGS. 2 and 3. Constriction may also be achieved by deformation of deformable zones inside the body of the said ring. Placing a slot however constitutes the simplest solution to achieve constriction, that is to say circular narrowing of the ring around the threaded rod or screw 4. Constriction takes place preferably by narrowing of the ring around the head or the end portion of threaded rod or screw 4 that is generally unthreaded. This smooth head may have any shape.

Two methods for using the embodiments of the invention may be envisaged.

In a first embodiment of the invention according to FIG. 1, the ring 3 is orientably mounted inside the hole 2 in the part 1. Furthermore, the ring 3 takes the shape of a ring having a generally spherical outer surface divided by a slot being housed inside a bore or aperture 2 generally spherical in cross-section in a shape complementary to the hole 2 of the part 1. The sphericity allows any axial orientation of the screw inside the hole to be achieved. Thus, the ring constitutes the equivalent of a pivot.

The front face of the ring 3 is provided with raised or projecting elements, such as the flutes 6, fitted to cooperate with a rotational drive tool for the ring 3. This ring 3 may be premounted in the hole 2 of the part 1, such premounting being done at the factory. This ring 3 may still be movably mounted in the hole 2 of the part 1. The threaded rod 4 comprises, on its free end for screwing, at least one cavity 7, recessed or raised, intended to cooperate with a screwdriving tool. In the example shown, this rod or screw 4 is provided, at its drive end, with a prismatic axial cavity suitable to receive the head of a rotational drive tool for the rod or screw 4 such as a hexagon socket.

The head of this threaded rod or screw is provided, at its drive end or in the vicinity of this latter, with a shoulder 8 which may rest after the screw is fully inserted on the front face of the ring 3 to allow mating of the part 1 with its support S. This shoulder is more specifically shown in FIG. 1. One of the advantages of this device is to be able to vary as needed the distance between part 1 and support S even though the locking of the threaded rod or screw 4 is guaranteed regardless of the nature or of the quality of the interface between part 1 and support S (plate and bone surface).

Figure 5:
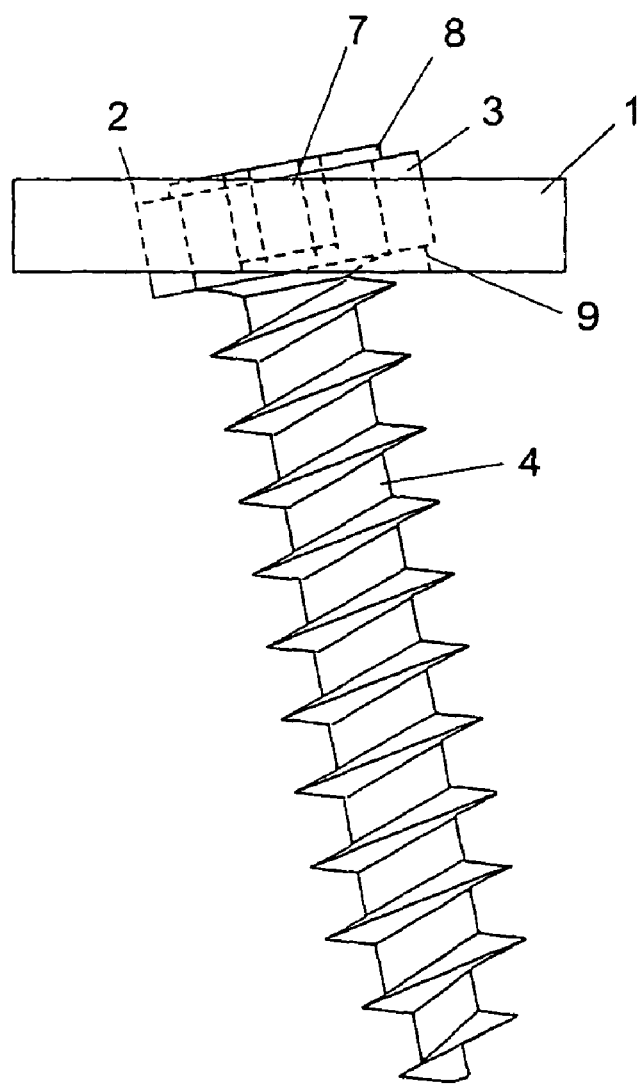
FIG. 5 is a front view partially in section of a second embodiment of a device according to the invention in unassembled state of the constituent elements.

In another embodiment of the invention shown in FIG. 5, the part 1 is provided with a pre-oriented hole provided with an internal shoulder 9 for retaining of the ring 3 inside the hole. This shoulder, housed in the bottom of the bore of the part 1, as a plate, retains the ring 3 during the compression phase of the plate on the bone during a return movement of the bone fragment.

The method of installation of one such device is the following. It consists of introducing the threaded rod or screw 4 into the ring 3, the latter already disposed in the hole 2 of the part 1. After screw threaded rod 4 is driven to its final position then ring 3 is rotationally driven to ensure, by constriction of the ring 3, immobilization of the screw in the hole 2. Thus the engagement of the high points of ring 3 engage the sides of aperture 2 and deforms inwardly to lock the screw.

In a more detailed fashion, the phases of the installation of rod 4 are generally the following. The surgeon at first carries out a forming of the plate to match the bone with special forceps maintaining the integrity of the bores in the plate. The plate is then positioned on the bone. A drill guide is introduced into the ring housed inside the plate to allow orientation of the ring based on the orientation that surgeon wishes the screw 4 to have. The surgeon then proceeds with drill using the drilling guide that allows positioning the axis of the threaded rod or screw in the axis of the ring in such a way that the axis of the rod or screw and axis of the ring are absolutely coincident. The drilled length is measured using a gauge. A threaded rod or screw of matching length is then chosen based on the length measured by the gauge. The screw is installed by rotational driving using a screwdriver. This screwing takes place until possible mating of the plate on the bone or drawing back of a bone segment by continuing to screw so the shoulder of screw head 8 is in contact with the front face of ring 3. The plate 1 comprising generally a plurality of holes each with a ring 3 and the group of screws is installed. Once the group of screws is positioned, all the screws can then be locked to the plate 1 by tightening ring 3 tightened by rotational driving of each ring using a fitted tool such as a spanner wrench.

In the use of one connecting device for solidly connecting the plate to the screw, no unscrewing, backward movement, or swiveling of the screw in its hole is noted. The screw is thus immobilized along directions of movement, namely the direction of backward movement, the rotation of the screw around its axis, and the axis of rotational immobilization around the center of the sphere i.e. in polyaxial movement. The radial force that is applied at the time of rotational driving of the ring between external wall of the ring and the inside wall of the hole 2, is preferably exerted at at least three points. There would be the four sites of the ring 3 of FIGS. 2 and 3 or the three raised radial portions of FIGS. 6 thru 8. Constriction is generally achieved by narrowing of the slot.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for connecting an osteosynthesis plate having at least one hole to a bone mass comprising at least one fixing element in the form of a threaded rod or screw passing through the hole, the hole housing a ring in the plate, said threaded rod to be screwed into the bone mass, the ring is a constrictive ring having a circular screw receiving bore having a central axis extending through the center of the bore in which a non-circular external profile of the ring cooperates with a non-circular internal profile of the hole of the plate to cause, during rotational movement of the ring in the hole, a constriction of the ring around a trailing end of the rod or screw ensuring the immobilization of the threaded rod and at the same time an immobilization by wedging of the ring in the hole, the ring external profile having at least two raised radial portions spaced at angular intervals around an outermost circumference of the external profile of the ring, the raised radial portions at a radial distance from the central axis of the screw receiving bore in the ring which distance is greater than the distance from the central axis of any portion of the outermost circumference intermediate the raised radial portions, the raised radial portions extending generally perpendicular to the central axis through the center of the screw receiving bore in the ring.

2. The device according to claim 1, wherein the ring is slotted.

3. The device according to claim 1, wherein the ring has an axis and is mounted inside the hole of the part in a manner wherein the axis of the ring is moveable within the hole.

4. The device according to claim 1, wherein the ring takes the form of a slotted ring having a generally spherical outer surface, said ring being housed inside a generally spherical surface in said hole, said surface complementary to an outer surface of said ring.

5. The device according to claim 1, wherein a front face of the ring is fitted with coupling elements shaped to cooperate with a rotational drive tool for the ring.

6. The device according to claim 1, wherein the ring is premounted in the hole of the plate.

7. The device according to claim 1, wherein said ring is movably mounted in the hole of the plate.

8. The device according to claim 1, wherein the trailing end of the threaded rod or screw has at least one coupling element intended to cooperate with a driving tool.

9. The device according to claim 5, wherein the threaded rod is provided, on its trailing end, with a shoulder, engagable with the front face of the ring.

10. The device according to claim 1, wherein the plate is provided with a pre-oriented hole provided with an internal shoulder for retaining of the ring inside the hole in the part.

11. A method of installation of a device for solidly connecting a part having at least one non-circular hole, to a support comprising inserting a split ring having a non-circular outer surface in said non-circular hole, the split ring outer surface having at least two raised radial portions spaced at regular angular intervals around an entire circumference of the split ring outer surface, the raised radial portions at a distance from a central axis of a screw receiving bore in the split-ring which distance is greater than the distance from the central axis of any portion of the outer surface intermediate the raised radial portions, the raised radial portions extending generally perpendicular to the central axis through the center of the screw receiving bore in the split ring;

introducing a screw into the screw receiving bore after the split ring disposed in the non-circular hole in the part driving the screw into the support to its final position then rotationally driving the split ring within the hole to cause engagement of the raised radial positions and the non-circular hole and constriction of the ring resulting from the engagement of the non-circular surfaces and the immobilization of the split ring in said hole.

12. A system for connecting a screw to a plate overlying a substrate comprising:

a non-circular aperture in said plate extending along a first axis;

a spilt-ring mounted in said aperture said split-ring having a non-circular outer surface and an internal bore extending along a central second axis, the ring outer surface having at least two raised radial portions spaced at angular intervals around an entire circumference of the outer surface, each raised radial portion at a distance from the second axis of the internal bore in the split-ring which is greater than the distance from the second axis to a portion of the outer surface intermediate the raised radial portion, the raised radial portion extending parallel to a plane of the top and bottom surface of the ring which planes are perpendicular to the second axis of the internal screw receiving bore in the ring a screw having a trailing end engagable with the internal bore in the split-ring and a threaded leading portion for engaging the substrate; and a tool for rotating said split-ring from a first position wherein said inner bore of said split-ring allows rotation of said screw to a second position wherein said non-circular outer surface of said split-ring lockingly engages said non-circular aperture in said plate and said inner bore of said split-ring compresses around said trailing portion of the screw to couple said screw to said plate.

13. The system as set forth in claim 12 wherein said screw trailing end has a circumferential wall extending parallel to a longitudinal axis of the screw, said wall for engaging the inner bore of said split-ring.

14. The system as set forth in claim 13 wherein said inner split-ring bore has a circumferential wall extending parallel to the longitudinal axis of said screw.

15. The system as set forth in claim 14 wherein the circumferential wall of said screw and said split-ring bore are in line to line contact.

16. The system as set forth in claim 1 wherein said screw trailing end has a circumferential wall extending parallel to a longitudinal axis of the screw, said wall for engaging an inner bore of said constrictive ring.

17. The system as set forth in claim 16 wherein said constrictive ring has a bore with a circumferential wall extending parallel to the longitudinal axis of said screw.

18. The method as set forth in claim 11 further comprising moving a central axis of a bore in the split-ring with respect to a central axis of the plate bore to form an angle therebetween.

19. The method as set forth in claim 18 wherein the split-ring has a generally spherical outer surface.

* * * * *